United States Patent [19]
Yarborough et al.

[11] Patent Number: 5,558,667
[45] Date of Patent: Sep. 24, 1996

[54] METHOD AND APPARATUS FOR TREATING VASCULAR LESIONS

[75] Inventors: J. Michael Yarborough, Tucson, Ariz.; R. Rox Anderson, Lexington, Mass.; George Marcellino, Los Gatos, Calif.; Gerald M. Mitchell, Tucson, Ariz.

[73] Assignee: Coherent, Inc., Santa Clara, Calif.

[21] Appl. No.: 369,465

[22] Filed: Jan. 6, 1995

Related U.S. Application Data

[63] Continuation-in-part of Ser. No. 355,512, Dec. 14, 1994, abandoned.

[51] Int. Cl.⁶ .............................. A61B 17/36; H01S 3/10
[52] U.S. Cl. .............................................. 606/9; 372/21
[58] Field of Search .................... 606/10, 11, 12, 606/2, 9; 372/21, 22, 101

[56] References Cited

U.S. PATENT DOCUMENTS

| | | | |
|---|---|---|---|
| 5,025,446 | 6/1991 | Kuizenga | 372/21 |
| 5,130,997 | 7/1992 | Ortiz et al. | 372/21 |
| 5,217,455 | 6/1993 | Tan | 606/9 |
| 5,282,797 | 2/1994 | Chess | 606/9 |
| 5,287,380 | 2/1994 | Hsia | 372/69 |
| 5,290,273 | 3/1994 | Tan | 606/9 |
| 5,304,170 | 4/1994 | Green | 606/9 |
| 5,312,395 | 5/1994 | Tan et al. | 606/9 |
| 5,312,396 | 5/1994 | Feld et al. | 606/11 |
| 5,344,418 | 9/1994 | Ghaffari | 606/9 |

FOREIGN PATENT DOCUMENTS

| | | | |
|---|---|---|---|
| 0075860 | 4/1983 | European Pat. Off. | A61B 17/36 |
| 0429297 | 5/1991 | European Pat. Off. | A61N 5/06 |
| 0527050 | 2/1992 | European Pat. Off. | A61N 5/06 |
| WO90/12545 | 11/1990 | WIPO | A61B 17/36 |
| WO91/13652 | 9/1991 | WIPO | A61N 5/06 |

*Primary Examiner*—Angela D. Sykes
*Assistant Examiner*—Sonya Harris-Ogugua
*Attorney, Agent, or Firm*—Limbach & Limbach L.L.P.

[57] ABSTRACT

An apparatus and method is disclosed for treating vascular lesions. In the preferred embodiment, an intracavity, frequency doubled Nd:YAG laser is used to generate output pulses having a duration of 0.5 to 10.0 milliseconds. This laser output is used to irradiate the lesions. The laser energy is absorbed in the blood of the vein, causing it to coagulate and collapse. The long pulse duration helps to minimize bleeding while controlling thermal damage to surrounding tissue.

5 Claims, 2 Drawing Sheets

METHOD AND APPARATUS FOR TREATING VASCULAR LESIONS

PRIOR APPLICATIONS

This application is a continuation-in-part of prior application Ser. No. 08/355,512, filed Dec. 14, 1994 abandoned May 25, 1995.

TECHNICAL FIELD

The subject invention relates to a method and apparatus for treating vascular lesions. In the subject invention, the vascular lesions are treated using a flashlamp pumped, intracavity doubled, solid state laser generating output pulses having a duration of 0.5 to 10 milliseconds.

BACKGROUND OF THE INVENTION

There has been significant interest in developing laser systems which can be used to treat various forms of vascular lesions. The type of vascular disorders that have been investigated include port wine stains, face veins, telangiectasis, and birth marks. A wide variety of medical laser systems have been proposed and introduced to treat these various disorders.

The prior art lasers were designed to generate an output wavelength which is absorbed by constituents in the blood. When the vein is irradiated, the blood is heated, causing thermal damage to the vein. The damaged vein will thrombose and collapse so that blood will no longer pass through the vein.

The most effective laser systems are designed to deliver a relatively high amount of energy in a short period of time. If the energy is delivered over too long a period, significant thermal damage will occur in regions beyond the vein being treated. In order to avoid this problem and generate higher powers in a short period of time, most prior art systems generated a pulsed output.

One common method of generating short, high energy pulses is to use a Q-switch. In a Q-switched laser, the gain medium is excited during an initial period when lasing does not occur. The Q-switch is then opened, allowing the energy stored in the gain medium to be coupled out of the resonator. Q-switched laser pulses, while having high energy, tend to be relatively short, on the order of tens of nanoseconds. One example of a Q-switched medical laser is disclosed in U.S. Pat. No. 5,217,455, issued Jun. 8, 1993 to Tan. This patent discloses a Q-switched, tunable solid state alexandrite laser which generates an output in the 600 to 1100 nanometer range. The duration of the q-switched pulses is 10 to 300 nanoseconds.

In addition to solid state lasers, tunable dye lasers have also been used for treatment of pigmented lesions. For example, U.S. Pat. No. 5,312,395, issued May 17, 1994, to Tan relates to a dye laser having an output of 345 to 600 nanometers. The patent suggests that the duration of the output pulses should be 500 nanoseconds or less.

In order to provide a wider range of treatment options, it has been suggested that medical laser systems include more than one type of laser. For example, PCT Application No. WO 91/13652, published Sep. 19, 1991, discloses a laser system where both an alexandrite laser and a dye laser are combined in one housing.

It has been recognized that it would be desirable to generate high power pulses having a duration longer than is available in prior art medical laser systems. This problem was addressed in U.S. Pat. No. 5,287,380, issued Feb. 15, 1994, to Hsia. This patent relates to a flash lamp pumped dye laser. A flashlamp power circuit is disclosed which ramps up the amplitude of the drive current in order to increase the pulse length above 500 microseconds. By using the approach in the Hsia patent, an output pulse of 640 microseconds was created.

The inventors herein believe that the effectiveness of the treatment can be further enhanced if the pulse width can be even further lengthened. More specifically, it is believed that when pulses widths on the order of 500 microseconds or less are used, the laser energy tends to boil the blood in the veins being treated. When the blood is boiled, there is rapid expansion, bleeding and immediate purpura (bruises).

In preliminary investigations, the inventors herein have shown that improved results can be achieved with pulse widths in excess of 500 microseconds. When longer pulse widths are used, the veins tend to be coagulated without boiling the blood. As noted above, there is an upper limit on the ideal pulse width, since longer pulses result in excess thermal damage beyond the treatment site. Therefore, it is believed than an ideal system would be able to generate output pulses having a duration between 0.5 and 10 milliseconds, at a wavelength which is absorbed in the blood and having sufficient power to coagulate the vein.

Accordingly, it is an object of the subject invention to develop a laser system which can generate a long pulse output with sufficient power to coagulate and collapse veins.

SUMMARY OF THE INVENTION

This object is achieved in the subject invention wherein a laser system is provided which is capable of generating pulses exceeding 0.5 milliseconds, having a wavelength of 532 nm which is readily absorbed in the blood and having an energy of at least 0.5 joules per pulse. The laser system includes a neodymium doped solid state gain medium having a fundamental output wavelength of 1.06 microns. In accordance with the subject invention, a non-linear crystal, such as KTP, is located in the resonator at a focal point of the circulating beam. The non-linear crystal functions to double the frequency of the fundamental wavelength and generate output pulses at 532 nm.

A flashlamp is used to energize the gain medium. In accordance with the subject invention, the flashlamp pulses are arranged to generate output pulses in excess of 0.5 milliseconds and preferably between 0.5 to 10 milliseconds. The energy per pulse is on the order of 0.5 to 3.0 joules. It has been shown that pulses of this character can be used to coagulate unwanted blood vessels with a minimum of bleeding and pain.

It should be noted that intracavity, frequency doubled Nd:YAG lasers have been used in the prior art to treat vascular lesions. However, to the applicants knowledge, those systems have been operated with a Q-switch to generate very short pulses having a high peak power. It is believed that the subject long pulse, intracavity doubled Nd:YAG is the first laser of this type to be used for this purpose.

Further objects and advantages of the subject invention will become apparent from the following detailed description taken in conjunction with the drawings in which:

DETAILED DESCRIPTION OF THE PREFERRED EMBODIMENT

Figure 1:
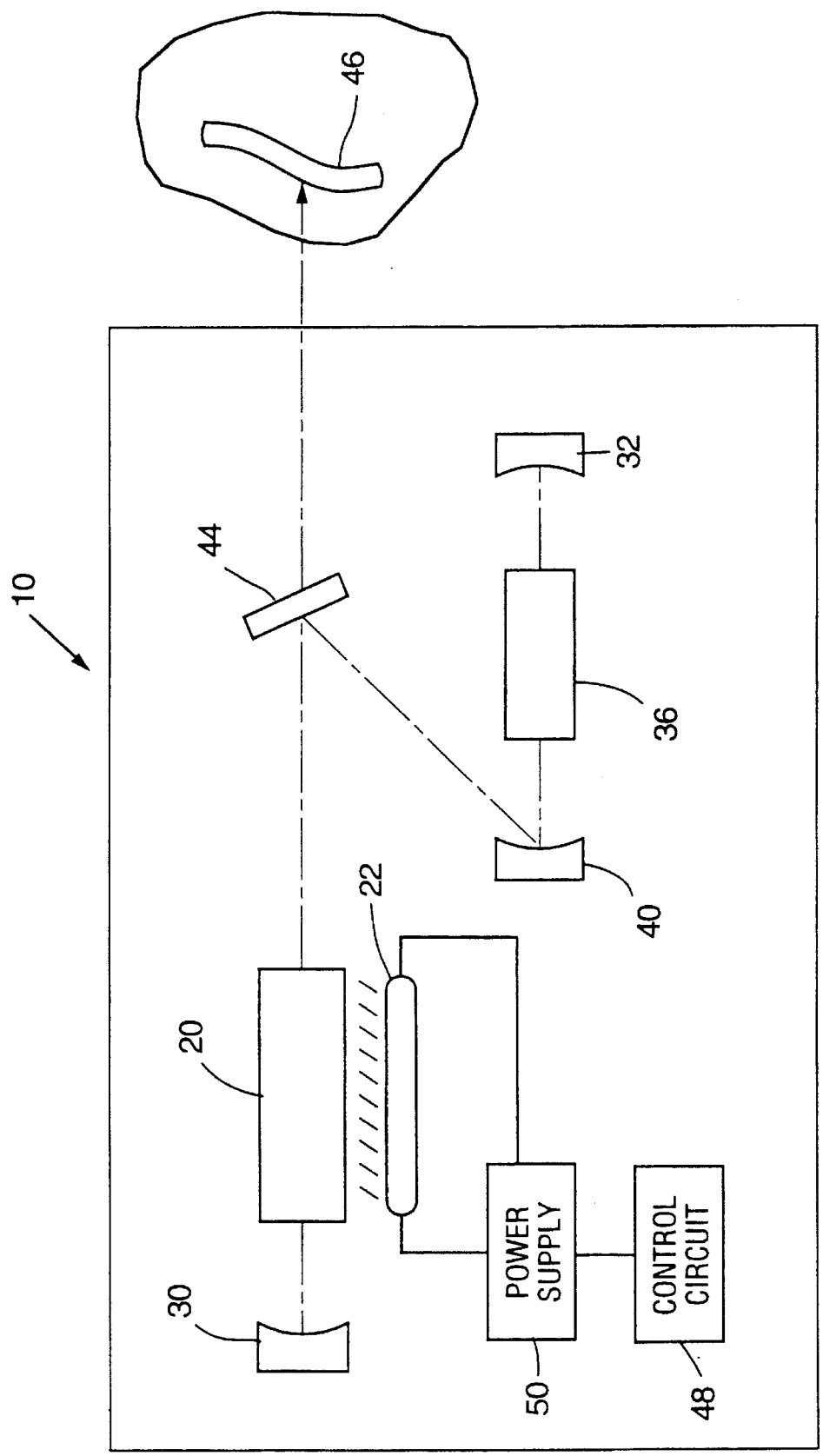
FIG. 1 is a simplified schematic diagram of the laser system of the subject invention.

Referring to FIG. 1, there is illustrated a schematic diagram of the laser 10 of the subject invention. The laser includes a neodymium doped solid state rod 20. The host crystal is preferably YAG, but could be any of the other standard hosts such as YLF and YSGG. When excited by a flashlamp 22, the Nd:YAG rod emits an output wavelength of 1.06 microns. This output is circulated within a resonant cavity bounded by highly reflective end mirrors 30 and 32.

Also included within the resonant cavity is a non-linear crystal 36. Non-linear crystal is provided to double the frequency of the fundamental wavelength generated by the Nd:YAG crystal 20. Suitable crystals for converting the 1.06 micron radiation into 532 nm light include KTP, BBO and KDP.

In the preferred embodiment, crystal 36 is located in a focusing branch of the resonator defined between curved end mirror 32 and curved mirror 40. It is desirable to focus the light within the crystal to increase the doubling efficiency.

Mirrors 30, 32 and 40 are provided with a coating which is highly reflective at both 1.06 microns and 532 nm. An output coupler mirror 44 is provided which is highly reflective at 1.06 microns and highly transmissive at 532 nm. By this arrangement, the doubling effect occurs through two passes through crystal 36. Light coupled out of the resonator through coupler 44 can be delivered to a vein 46 at the treatment site through either a fiber optic element or a hollow waveguide channel.

A control circuit 48 is provided for regulating the power supply 50. In operation, the control circuit will signal the power supply to energize the flashlamp. In the preferred embodiment, the flashlamp drive pulses have a duration between 0.5 and 10.0 milliseconds. At these pulse widths, a significant amount of intracavity power can be built up to enhance the efficiency of the doubling process.

Figure 2:
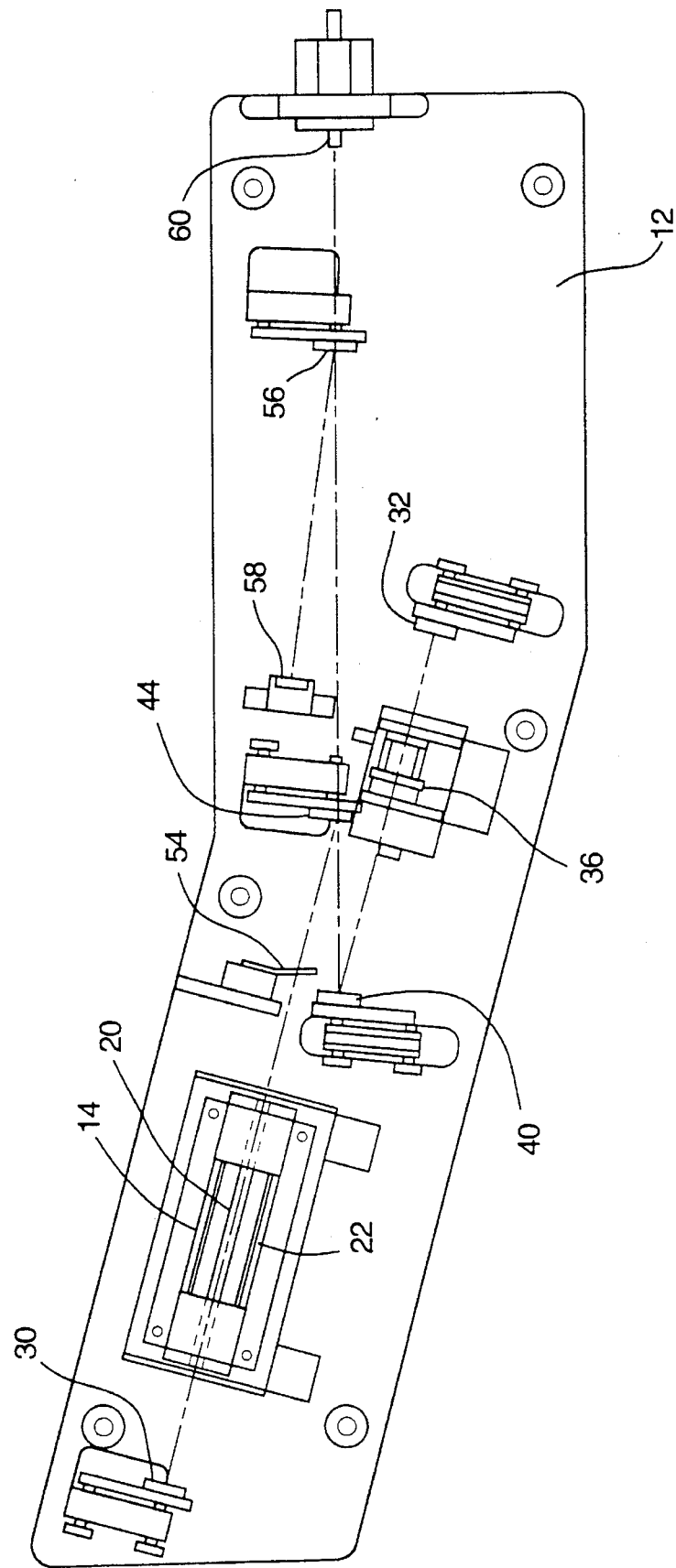
FIG. 2 is a top plan view of a preferred form of the laser system of the subject invention.

FIG. 2 is top plan view of the lay out of the preferred form of the subject invention. The optical elements of the laser are mounted on a housing 12. A laser head 14 includes a Nd:YAG rod 20 and the flashlamp 22. The flashlamp and rod are water cooled with a circulation system in a conventional manner.

The gain medium 20 lies within the resonator defined by curved mirrors 30 and 32. The spacing of the mirrors is set to optimize performance at 1.06 microns. The non-linear crystal 36 is located within a focusing branch of the resonator defined by end mirror 32 and curved fold mirror 40. Each of these mirrors includes a coating is which highly reflective at both 1.06 microns and 532 nm. A flat output coupler 44 is provided which is highly reflective (about 98%) at 1.06 microns and highly transmissive at 532 nm.

A shutter 54 is provided in the cavity which is selectively positionable into the path of the laser beam. Upon start-up, the shutter is oriented to block the beam. During the first second or two of flashlamp operation, the gain medium 20 will become heated and any thermal lens effects will tend to stabilize. Once the thermal gradients in the gain medium have stabilized, the shutter is moved and the beam is permitted to reach the crystal 36. In this manner, the damage to the crystal from hot spots created by thermal lensing in the gain medium during warm-up is minimized. The use of the shutter also results in a more stable output.

A reflective filter 56 is mounted on the housing 12 to reject any 1.06 micron radiation which is transmitted past the output coupler. This portion of the beam is captured by a beam dump 58. The output beam is then directing into a fiber focus assembly 60 which includes an adjustable lens for injecting the laser output into a fiber.

Unlike prior art Q-switched system, which generate very short, high peak power pulses, the pulses generated by the subject system are longer and have lower peak power. For this reason, the doubling efficiency is less than with Q-switched lasers. In tests with the subject system, it is estimated that the doubling efficiency is on the order of 1 to 2 percent. Nonetheless, the subject system has been designed to generate pulses having an energy from 0.5 to 3.0 joules. At the longer pulse widths available from the subject system, high power pulses can be generated. For example, a one joule, two millisecond pulse will produce 500 watts of peak power.

The subject system has been used experimentally in animal studies. In the animal studies, albino rabbits were anesthetized by intramuscular injection of ketamine. The fur was depilated from the dorsal ear surfaces with Neet. Peripheral ear venules were selected and their diameters measured under a dissecting microscope. Marker dots were placed on either side of each venule at the site to be exposed to the laser. These assured accurate laser exposure placement and orientation for histological sectioning perpendicular to the venule.

In each animal, laser exposures were performed in duplicate for 160 and 320 µm vessels. The exposure durations were one, five and ten milliseconds. The fluences varied between 10 and 20 J/cm$^2$. Each exposed vessel was observed immediately and at five and ten minutes for responses including vasodilation, vasoconstriction, apparent flow changes, closure and hemorrhage. Two to three hours after exposure, the sites were biopsied and fixed in formalin for routine processing and light microscopic histology after staining with hematoxylin/eosin stains.

Laser pulses of five to ten milliseconds at fluences between 10 and 15 J/cm$^2$, caused clinically a vasoconstriction reaction in the targeted vessels. Histologically, the endothelial cells in these vessels were damaged and polymorphonuclear cells stuck to the interior vessel wall. The red blood cells showed partial or complete agglutination. The vessels were also surrounded by a fine rim of perivascular collagen denaturation. Polarized microscopy showed that the damaged collagen had also lost is birefringence. At 20 J/cm$^2$, the vascular injury was similar, but there was pronounced epidermal and adjacent collagen damage. This was prevented by cooling of the skin during laser exposures with a cooling chamber.

Based on the above, it can be seen that the subject laser produces an ideal output format for treating various vascular lesions. The longer pulse width tends to significantly reduce purpura while still minimizing thermal damage to surrounding tissue.

Based on the results described above, the following general treatment parameters can be defined for use in human patients.

PULSE DURATION (Pulsewidth)

The ideal pulse duration for treating most portwine stains (PWS) and small telangiectasia is 1–10 milliseconds. This corresponds to thermal relaxation times of vessels approximately 30–100 micron diameter, typical for PWS lesions. This pulse duration therefore achieves thermal confinement on the order of the vessels, but less mechanical damage and hemorrhage than for sub-millisecond (e.g., pulsed dye laser) pulses. The 1–10 millisecond pulse duration also allows heat flow into the vessel wall during the response time, increasing effectiveness of vessel wall coagulation.

FLUENCE

The fluence needed for treatment with this laser lies between those typically used with the sub-millisecond 585 nm dye lasers (58 Joules/cm$^2$) and those typically used with longer duration exposures from argon, krypton, argon-dye, copper vapor, or KTP lasers (25–40 Joules/cm$^2$). As with dye lasers, the ideal fluence also varies inversely with the exposure spot diameter, for spots less than about 5 mm, and with skin melanin content (pigmentation). The ideal fluence is typically 12–20 Joules/cm$^2$ for spots of 3 mm somewhat higher for spots less than 3 mm, in most Caucasians.

PULSE REPETITION RATE

Exposures are produced contiguously on the skin. For manual placement, a repetition rate of up to about 10 Hz is controllable. For speed of operation, a rate of at least 1 Hz is desirable.

OVERLAPPING PULSES

One method of application practical with this laser is overlapping (multiple) pulses to a given skin site. Two modes can be used. When at least 10 seconds are allowed for bulk cooling between pulses, thermal damage can remain selective for vessels. If gross coagulation is desired, however, multiple pulses can be delivered faster, e.g., at 1–10 Hz until a grey-white color change indicating gross coagulation is seen.

While the subject invention has been described with reference to a preferred embodiment, various changes and modifications could be made therein, by one skilled in the art, without varying from the scope and spirit of the subject invention as defined by the appended claims.

We claim:

1. A method of treating vascular lesions with an intracavity doubled solid state laser, said laser having a neodymium doped solid state gain medium and a flashlamp for optically pumping the gain medium comprising of steps of:

energizing the flashlamp with pulses having a duration between 0.5 and 10.0 milliseconds and a wavelength of 532 nm; and irradiating the lesion with said output pulses at a fluence level in excess of 1 joules/cm$^2$.

2. A method as recited in claim 1 wherein said pulses have a duration between 5.0 and 10 milliseconds.

3. A method as recited in claim 1 wherein said fluence level is in excess of 10 joules/cm$^2$.

4. A method as recited in claim 1 wherein said fluence level is between 10 and 20 joules/cm$^2$.

5. A method as recited in claim 1 wherein said pulses have a repetition rate greater than 1 Hz.

* * * * *

UNITED STATES PATENT AND TRADEMARK OFFICE
CERTIFICATE OF CORRECTION

PATENT NO. : 5,558,667
DATED : September 24, 1996
INVENTOR(S) : J. Michael Yarborough, et al.

It is certified that error appears in the above-indentified patent and that said Letters Patent is hereby corrected as shown below:

Column 6, line 14, after "10.0 milliseconds" add --to generate frequency doubled output pulses having a duration between 0.5 milliseconds and 10 milliseconds--

Signed and Sealed this

Thirty-first Day of December, 1996

Attest:

BRUCE LEHMAN

*Attesting Officer*  *Commissioner of Patents and Trademarks*